US012232854B2

(12) United States Patent
Aldar (10) Patent No.: US 12,232,854 B2
(45) Date of Patent: Feb. 25, 2025

(54) ORAL ECG DEVICE

(71) Applicant: OMNYSENSE LTD., Tel-Aviv (IL)

(72) Inventor: Yossi Aldar, Tel-Aviv (IL)

(73) Assignee: OMNYSENSE LTD., Tel-Aviv (IL)

( * ) Notice: Subject to any disclaimer, the term of this patent is extended or adjusted under 35 U.S.C. 154(b) by 581 days.

(21) Appl. No.: 17/620,876

(22) PCT Filed: Aug. 11, 2020

(86) PCT No.: PCT/IL2020/050874
§ 371 (c)(1),
(2) Date: Dec. 20, 2021

(87) PCT Pub. No.: WO2020/255149
PCT Pub. Date: Dec. 24, 2020

(65) Prior Publication Data
US 2022/0313100 A1    Oct. 6, 2022

Related U.S. Application Data

(60) Provisional application No. 62/863,890, filed on Jun. 20, 2019.

(51) Int. Cl.
*A61B 5/0205*    (2006.01)
*A61B 5/00*    (2006.01)
(Continued)

(52) U.S. Cl.
CPC .......... *A61B 5/02055* (2013.01); *A61B 5/002* (2013.01); *A61B 5/0533* (2013.01);
(Continued)

(58) Field of Classification Search
CPC ....... A61B 5/02055; A61B 5/282; A61B 5/26; A61B 5/25; A61B 5/002; A61B 5/0533;
(Continued)

(56) References Cited

U.S. PATENT DOCUMENTS 9,161,697 B2    10/2015    Azimi
2010/0234746 A1    9/2010    Sebelius
(Continued)

FOREIGN PATENT DOCUMENTS

CN    103584871 A    2/2014
CN    205107641 U    3/2016
(Continued)

OTHER PUBLICATIONS

Mody et al. Fever-induced electrocardiographic changes. J Gen Intern Med. Jan. 2015;30(1):136-7. doi: 10.1007/s11606-014-2992-9. Epub Sep. 10, 2014. PMID: 25205622; PMCID: PMC4284273.
(Continued)

*Primary Examiner* — Linda C Dvorak
*Assistant Examiner* — Abigail Bock
(74) *Attorney, Agent, or Firm* — The Roy Gross Law Firm, LLC; Roy Gross (57) ABSTRACT

The present invention relates to a 1- or 3-lead oral ECG device, shaped and implemented like a household digital thermometer. The 3-lead device comprises three contact electrodes: two contact electrodes on a body of the device, configured for contact with the left and right hands; and one contact electrode on a metallic tip of the device—which may comprise a thermometer—configured for contact with the mouth. The 1-lead device comprises any two of these three contact electrodes and a temperature sensor disposed in the metallic tip. A novel transformation of the three leads from the 3-lead device enables the ECG signals to be processed like a standard ECG that comprises a contact electrode in contact with the leg instead of the mouth. An oral ECG device of the invention may comprise other sensors, such as a pulse-oximetry sensor, respiratory rate sensor, skin temperature sensor, body impedance sensor, galvanic skin response sensor, and/or blood-flow sensor.

11 Claims, 5 Drawing Sheets

(51) Int. Cl.

| | |
|---|---|
| *A61B 5/0533* | (2021.01) |
| *A61B 5/08* | (2006.01) |
| *A61B 5/1455* | (2006.01) |
| *A61B 5/25* | (2021.01) |
| *A61B 5/26* | (2021.01) |
| *A61B 5/282* | (2021.01) |
| *A61B 5/332* | (2021.01) |
| *G16H 40/67* | (2018.01) |
| *G16H 50/20* | (2018.01) |

(52) U.S. Cl.
CPC ........ *A61B 5/0816* (2013.01); *A61B 5/14552* (2013.01); *A61B 5/25* (2021.01); *A61B 5/26* (2021.01); *A61B 5/282* (2021.01); *A61B 5/682* (2013.01); *G16H 40/67* (2018.01); *G16H 50/20* (2018.01); *A61B 5/332* (2021.01); *A61B 2560/045* (2013.01); *A61B 2562/0271* (2013.01)

(58) Field of Classification Search
CPC ... A61B 5/0816; A61B 5/14552; A61B 5/682; A61B 5/332; A61B 2560/045; A61B 2562/0271; G16H 40/67; G16H 50/20
See application file for complete search history.

(56) References Cited

U.S. PATENT DOCUMENTS

| | | |
|---|---|---|
| 2013/0035602 A1 | 2/2013 | Gemer |
| 2013/0253286 A1 | 9/2013 | Fridman |
| 2015/0045629 A1 | 2/2015 | Azimi |
| 2016/0135701 A1 | 5/2016 | Drake |
| 2016/0287128 A1 | 10/2016 | Jain et al. |
| 2018/0098620 A1 | 4/2018 | Lee et al. |
| 2018/0110418 A1 | 4/2018 | Fridman et al. |

FOREIGN PATENT DOCUMENTS

| | | |
|---|---|---|
| CN | 205493819 U | 8/2016 |
| CN | 106999082 A | 8/2017 |
| EP | 2835100 B1 | 2/2015 |

OTHER PUBLICATIONS

Papadatou-Pastou et al. Human handedness: A meta-analysis. Psychol Bull. Jun. 2020;146(6):481-524. doi: 10.1037/bul0000229. Epub Apr. 2, 2020. PMID: 32237881.

Extended European Search Report for European Patent Applicant No. 20826070.3, dated Jun. 20, 2022, 11pp.

Nelwan, S. P. et al. "Correction of ECG variations due to non-standard electrode positions." Computers in Cardiology 2001. vol. 28 (Cat. No. 01CH37287). IEEE, 2001. Sep. 26, 2001; doi: 10.1109/CIC.2001.977656.

Mason et al. "Recommendations for the standardization and interpretation of the electrocardiogram: part II: the electrocardiogram and its technology a scientific statement from the American Heart Association Electrocardiography and Arrhythmias Committee, Council on Clinical Cardiology; the American College of Cardiology Foundation; and the Heart Rhythm Society endorsed by the International Society for Computerized Electrocardiology." Journal of the American College of Cardiology 49.10 (2007): 1109-1127. Mar. 13, 2007; DOI: 10.1161CIRCULATIONAHA.106.180201.

PCT International Search Report for International Application No. PCT/IL2020/050874, mailed Nov. 19, 2020, 4pp.

PCT Written Opinion for International Application No. PCT/IL2020/050874, mailed Nov. 19, 2020, 6pp.

Papadatou-Pastou, M. et. al. (2020). Human handedness: A meta-analysis. PsychologicalBulletin. 146 (6): 481-524.; Retrieved Dec. 20, 2021 from: https://doi.org/10.1037/bul0000229.

Mody, P. et al. (2015). Fever-Induced Electrocardiogramhic Changes. J Gen Intern Med. Jan. 2015; 30(1): 136-137. Published online Sep. 10, 2014. doi: 10.1007/s11606-014-2992-9. PMCID: PMC4284273.

The State Intellectual Property Office of People's Republic of China, First Office Action for Chinese Patent Application No. 2020800577578, dated Oct. 19, 2021, 21pp.

ORAL ECG DEVICE

CROSS REFERENCE TO RELATED APPLICATIONS

This application is a National Phase of PCT Patent Application No. PCT/IL2020/050874 having International filing date of Aug. 11, 2020, which claims the benefit of priority of U.S. Provisional Patent Application No. 62/863,890, filed Jun. 20, 2019, the contents of which are all incorporated herein by reference in their entirety.

FIELD OF THE INVENTION

The invention is in the field of home diagnostic medical devices, and in particular to an ECG device usable like a household thermometer.

BACKGROUND TO THE INVENTION

Home medical devices that measure one or more vital parameters, including ECG, are disclosed in the prior art:

US2018/0110418A discloses a self-contained hand-held device. The device can obtain all vital signs +ECG and pulse-ox by being held by the patient for approximately half a minute. The device contains sensors on the hand-held unit as well as on the individual/disposable mouthpiece. The method of the present invention includes simultaneously acquiring the following measurements: temperature, pulse rate, breathing rate, blood pressure, electrocardiogram, heart rate and pulse-ox waveform and blood oxygen level.

US2013/0253286 discloses an intraoral multisensor device that includes a mouthpiece, a plurality of sensors at least one of attached to or integrated with the mouthpiece, and a data communications unit configured to receive signals from the plurality of sensors. The mouthpiece has a form to permit stable arrangement at least partially within a person's mouth such that it can remain for hands-free sensing of a plurality of biological parameters. Also, an intraoral multisensor system includes an intraoral multisensor device and a data processing device adapted to communicate with the intraoral multisensor device.

The present invention advances the state-of-the-art in multi-functional home medical devices, as further described below.

SUMMARY

A number of different types of ECG exist. The simplest is the 2-contact, 1-lead ECG, which is typically measures between the left hand and the right hand. More complex versions include a 3-contact 3- or 6-lead ECG, 12-lead ECG and 15-lead ECG. In order to increase the likelihood that arrhythmias, ventricular fibrillation, atrial fibrillation etc. will be detected, it is preferable to have at least a 3-lead ECG trace for a physician to analyze.

Applying a 3-lead ECG to the body is relatively more cumbersome than a 1-lead ECG as the third contact needs to be attached to the left leg. This requires some sort of cable to be extended from the device to the leg or lower abdomen, and some form of electrode to be attached to the foot or elsewhere on the leg or lower abdomen.

Unlike the thermometer— which is the one medical device present in most homes in the developed world—the use of an ECG at home is unfamiliar and requires some kind of learning curve. There is therefore a need to provide a simple form of ECG which is easy to use and exploits the familiar thermometer format; and where both types of readings—temperature and ECG—are performed at the same time.

It is within the scope of the present invention to provide an oral 3-lead ECG device in the shape of a digital-thermometer comprising three contact electrodes:
  a left-hand contact electrode configured for contact with the left hand of a subject;
  a right-hand contact electrode configured for contact with the right hand of the subject; and
  a mouth contact electrode disposed on a metallic tip of the device, configured for contact with the patient's mouth;
  wherein the device further comprises a processor configured to perform a transformation of signals from lead II and lead III, terminating at the mouth contact electrode, thereby producing ECG traces mimicking traces of a standard ECG whose lead II and lead III terminate at a left-leg electrode.

It is further within the scope of the present invention to provide the abovementioned oral 3-lead ECG device, wherein the processor is configured to perform the transformation by
  transposing the order of Leads II and III;
  reversing the polarity and increasing the gain of the waveform of Lead II, and
  reversing the polarity of the waveform of Lead III.

It is further within the scope of the present invention to provide any one of the abovementioned oral 3-lead ECG devices, further comprising one or more sensors from a group consisting of an oral temperature sensor disposed in the metallic tip, a pulse-oximetry sensor, a respiratory rate sensor, a skin temperature sensor, a body impedance sensor, a galvanic skin response sensor, and a blood-flow sensor.

It is further within the scope of the present invention to provide the previous oral 3-lead ECG devices, wherein the pulse-oximetry sensor is positioned proximate to or opposite the left-hand contact electrode or right-hand contact electrode.

It is further within the scope of the present invention to provide any one of the abovementioned oral 3-lead ECG devices, further comprising a communications module enabling the display of the ECG trace on an external device (e.g., smartphone or computer).

It is further within the scope of the present invention to provide the previous oral 3-lead ECG device, wherein the display further comprises sensor data from one or more sensors from the group consisting an oral temperature sensor, a pulse-oximetry sensor, a respiratory rate sensor, a skin temperature sensor, a body impedance sensor, a galvanic skin response sensor, and a blood-flow sensor; and the oral 3-lead ECG device further comprises the one or more sensors.

It is further within the scope of the present invention to provide any one of the previous two oral 3-lead ECG devices, further comprising a data-transfer agent module installed in the external device, the data-transfer agent module configured to transmit the ECG and/or sensor data over the Internet to a remote device (e.g., for storage and/or analysis).

It is further within the scope of the present invention to provide the previous oral 3-lead ECG device, further comprising a remote agent module installed in the remote device; the remote agent module is configured to perform medical analysis of the transmitted ECG data and/or the transmitted sensor data.

It is further within the scope of the present invention to provide any one of the previous two oral 3-lead ECG devices, comprising either:

an ECG circuit with three ECG channels configured for simultaneously sampling the three leads; or an ECG circuit with one ECG channel, said ECG circuit configured for simultaneously sampling the three leads.

It is further within the scope of the present invention to provide a method for transformation of the signals from ECG leads of an oral 3-lead ECG, comprising steps of obtaining ECG traces from any one of the abovementioned oral 3-lead ECG devices;

transposing the order of Leads II and III;

reversing the polarity and increasing the gain of the waveform of Lead II; and reversing the polarity of the waveform of Lead III.

DETAILED DESCRIPTION

Figure 1A:
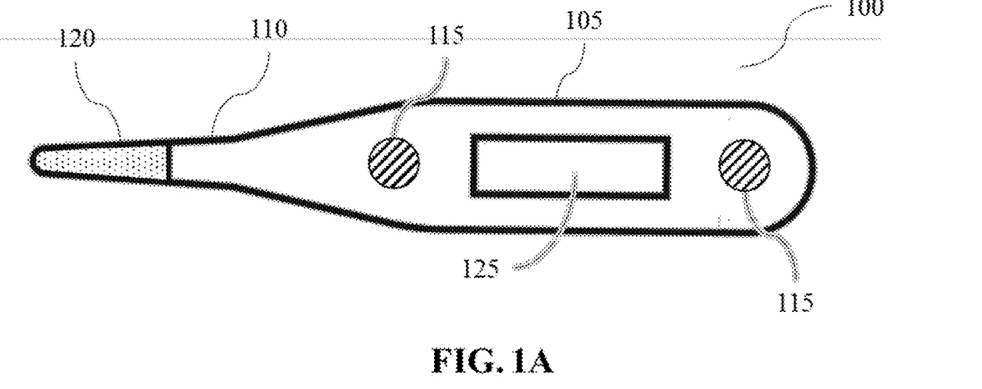
FIGS. 1A-1C each show a 1-lead oral ECG/thermometer device, according to some embodiments of the invention.
Figure 1B:
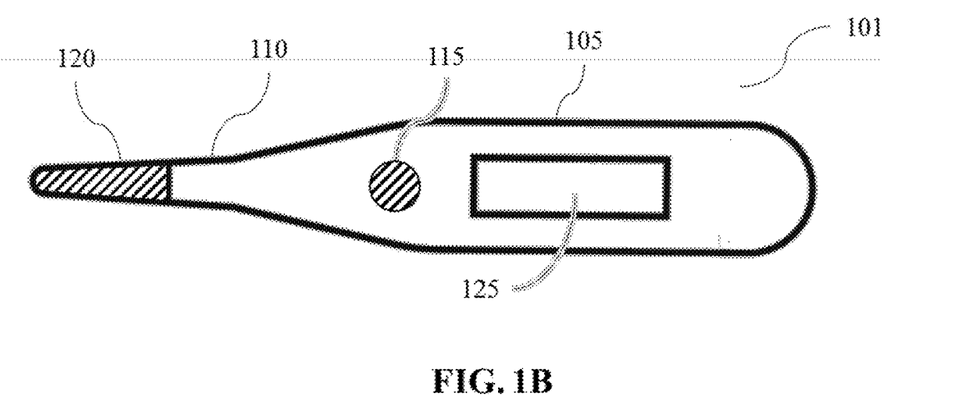
Figure 1C:
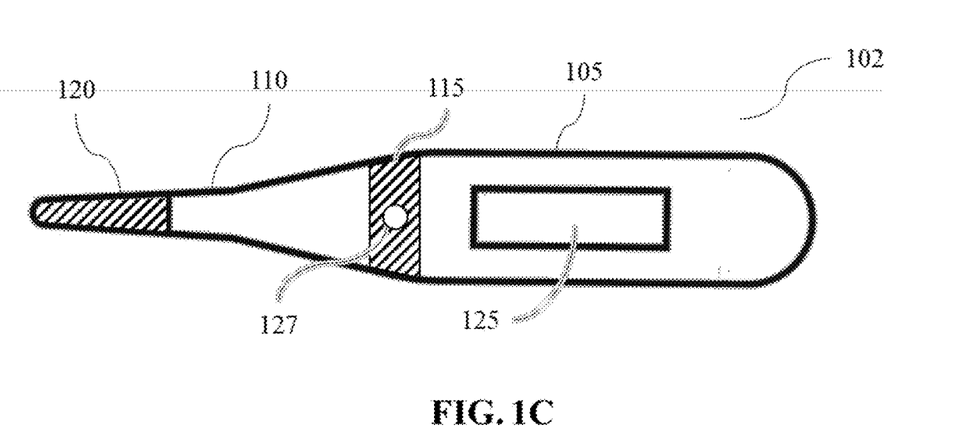

Reference is now made to FIGS. 1A-1C, each showing an oral 1-lead ECG/thermometer 100, according to some embodiments of the invention.

A device of the present invention comprises a thermometer-shaped device 100 comprising a body 105 and a neck 110. The body 105 contains at least one contact electrode 115, which can be circular as shown or any other shape. A contact electrode 115 may be disposed on the floor of a surrounding indent; the indent can serve as a guide for placement of a finger on the contact electrode 115. Contact electrodes 115 may be disposed on the front of the device, as shown. Alternatively, one or more of the contact electrodes 115 may be disposed on the reverse side of the device, such that a thumb is placed on a contact electrode 115. The neck 110 comprises a thermally and electrically conductive (typically metallic) tip 120 having a temperature sensor within, for measuring body temperature. In preferred embodiments, the body 105 further comprises a display 125 such as an LCD display, which can show at least body temperature. FIG. 1A shows an embodiment device 100 in which there are two contact electrodes 115 on the body 105. A 1-lead ECG circuit (internal to the device 100) connects to the two contact electrodes 115—configured for contact with two hands—and derives a 1-lead ECG trace. FIG. 1B shows an embodiment device 101 in which there is only one contact electrode 115 on the body 105. A 1-lead ECG circuit connects between the contact electrode 115 and the metallic tip 120.

A potential advantage of monitoring ECG and temperature is that a fever is known to cause electrocardiographic changes that can mimic life-threatening conditions [Mody, P., Pandey, A. & Joglar, J. Fever-Induced Electrocardiographic Changes. *J GEN INTERN MED* 30, 136-137 (2015)]. An elevated body temperature measured by the device 100 can therefore serve as an indication that the ECG trace generated by the device 100 is less reliable.

FIG. 1C shows an embodiment device 102 in which a pulse oximetry sensor 127 is disposed proximate to a contact electrode 115, such that the patient's hand is in contact with 170 both the contact electrode 115 and the pulse oximetry sensor 127. For example, the pulse oximetry sensor 127 may be disposed within a contact electrode 115, as shown, or adjacent to a contact electrode 115. In embodiments with a contact electrode 115 on the reverse side for contact with a thumb, the pulse oximetry sensor 127 can be disposed opposite to the reverse-side contact electrode 115, for placement by a finger opposing the thumb.

The pulse oximetry sensor 127 provides additional function to the device 100 while also enabling ECG-pulse oximeter sensor fusion, for example to provide cross-verification between the ECG and pulse oximetry sensor 127.

Figure 2:
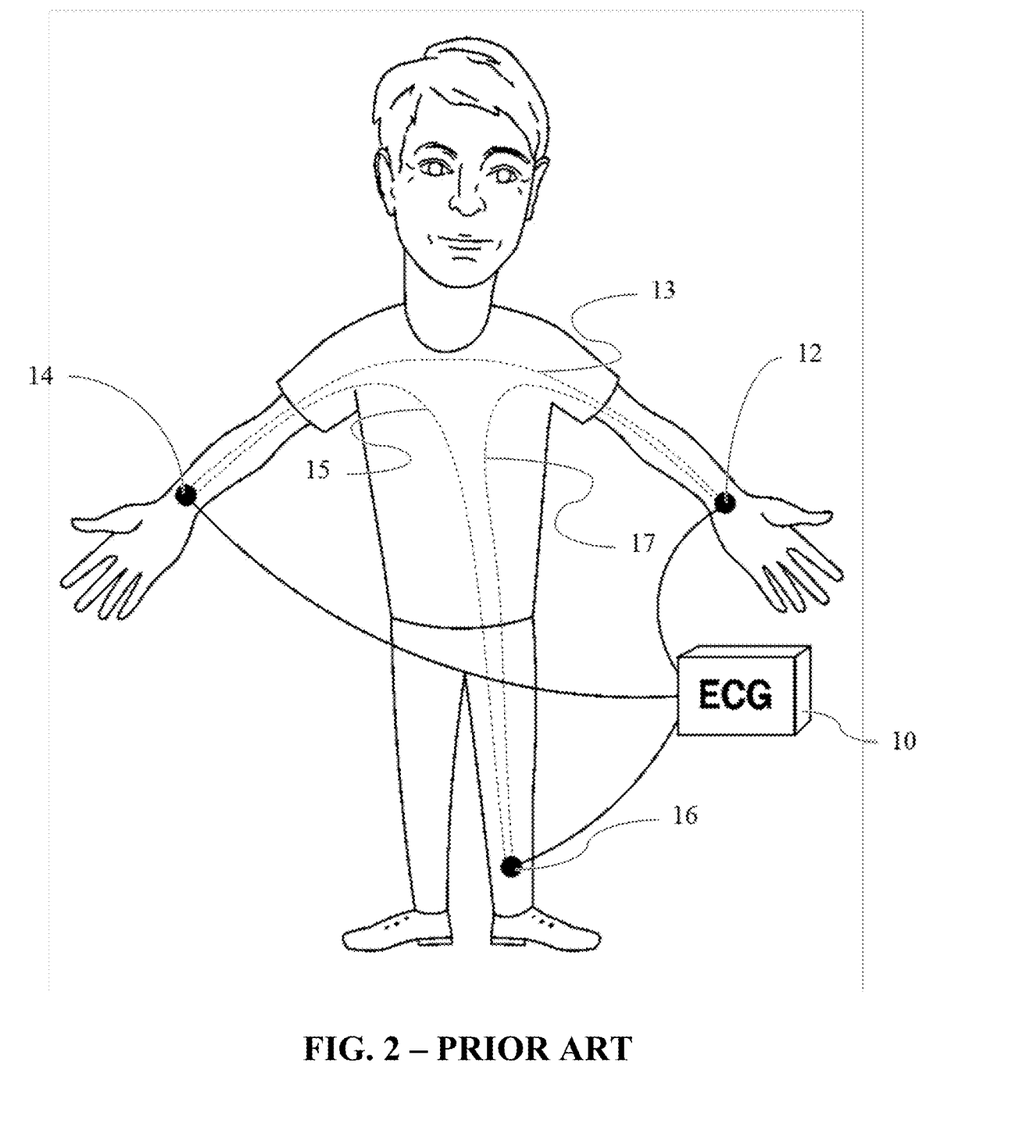
FIG. 2 shows a usage configuration of a standard 3-lead ECG of the prior art.

Reference is now made to FIG. 2, a usage configuration of a 3-lead ECG according to the prior art, where a standard-type ECG device 10 is connected by means of three electrodes to the standard locations on the body surface; namely Lead I 13 is between the right-hand electrode 14 and the left-hand electrode 12, Lead II 15 is between the right-hand electrode 14 and the left-leg electrode 16, and Lead III 17 is between the left-hand electrode 12 and the left-leg electrode 16.

Figure 3:
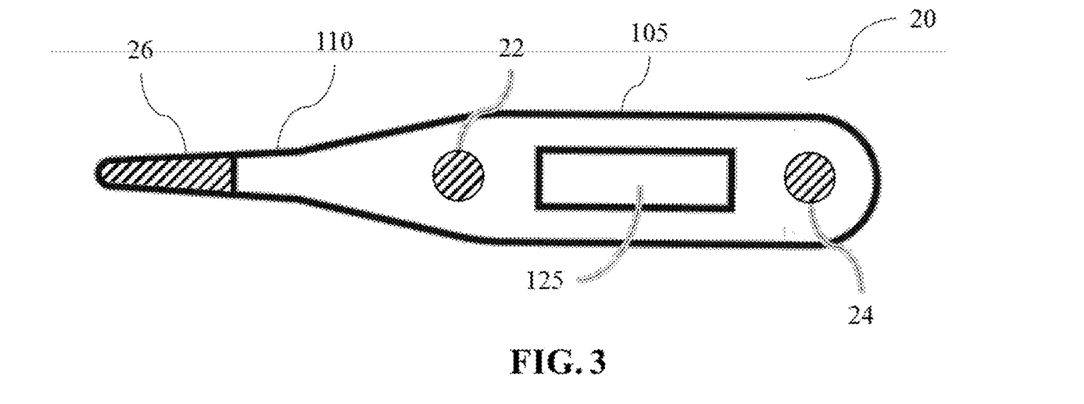
FIG. 3 shows an oral 3-lead ECG device according to some embodiments of the invention.

Reference is now made to FIG. 3, an oral 3-lead ECG device 20 according to some embodiments of the invention. The device 20 comprises a thermometer-shaped device 20 comprising a body 105 and a neck 110. The body 105 contains two contact electrodes: a right-hand contact electrode 24 and a left-hand contact electrode 22. The neck 110 contains a mouth contact electrode 26. Either or both hand contact electrodes 22, 24 may be disposed on the floor of a surrounding indent; the indent can serve as a guide for placement of a finger on the contact electrode 22, 24. The hand contact electrodes 22, 24 may be disposed on the front of the device, as shown. Alternatively, either or both of the hand contact electrodes 22, 24 may be disposed on the reverse side of the device, such that a thumb is placed on a hand contact electrode 22, 24. The device may further comprise a pulse oximetry sensor, disposed proximate to or opposite a hand contact electrode 22, 24 (see FIG. 1C, 115 and 127, and description pertaining thereto), thereby providing additional function to the device 100 while also enabling ECG-pulse oximeter sensor fusion. For example, to provide cross-verification between the ECG and pulse oximetry sensor, such as comparing the pulse rate obtained from the pulse oximetry waveform and the heart rate calculated from the ECG waveform. The neck 110 may further contain a temperature sensor within, for measuring body temperature. In preferred embodiments, the body 105 further comprises a display 125 such as an LCD display, which can show at least body temperature.

Figure 4:
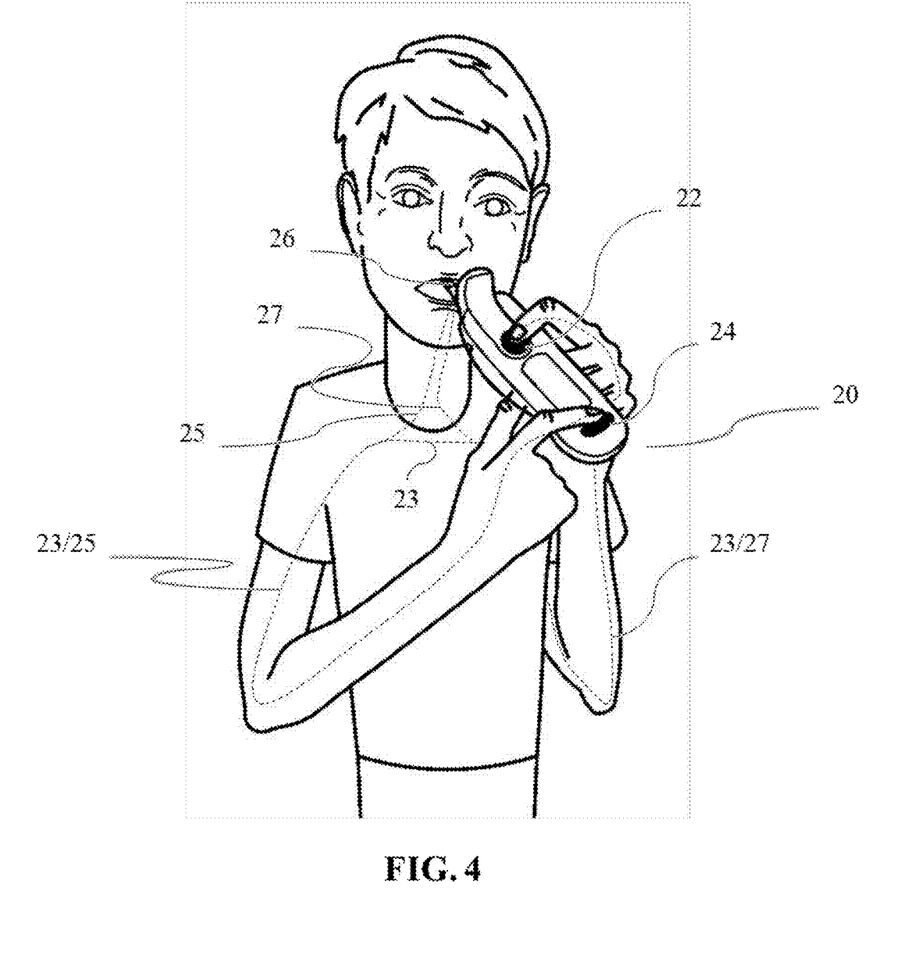
FIG. 4 shows a usage arrangement of an oral 3-lead ECG device, according to some embodiments of the invention. The dashed lines represent ECG leads. The dashed lines are for illustrative purposes, and are not intended to trace or suggest actual electrical paths of the leads.

Reference is now made to FIG. 4, showing a usage arrangement of the oral 3-lead ECG device 20. The right hand is positioned on the right-hand contact electrode 24 and the left hand is positioned on the left-hand contact electrode 22. The mouth contact electrode 26—corresponding to the left-leg electrode 16 of the leg-attached three-lead ECG 10—is positioned in contact with the mouth. In this arrangement, Lead I 23 is between the right-hand contact electrode 24 and the left-hand contact electrode 22, Lead II 25 is between the right hand contact electrode 24 and the mouth contact electrode 26, and Lead III is between the left-hand contact electrode 22 and the mouth contact electrode 26. As is clear from the figure, the mouth contact electrode 26 is implemented as a contact located at or near the patient's mouth, for example on the lips, the philtrum or under the tongue. In a preferred embodiment of the invention, the mouth contact electrode 26 is a metallic component such as a metal tip of the temperature sensor.

Surprisingly, even though the two configurations shown in FIG. 3 and FIG. 5 are significantly different, our team determined that a transformation of the signals received could be implemented such that the ECG trace produced post-transformation is substantively equivalent to a trace that would have been produced had an ECG device been connected in the standard fashion. The present invention comprises the thermometer-shaped ECG device described above in conjunction with the transformation approach.

Figure 5A:
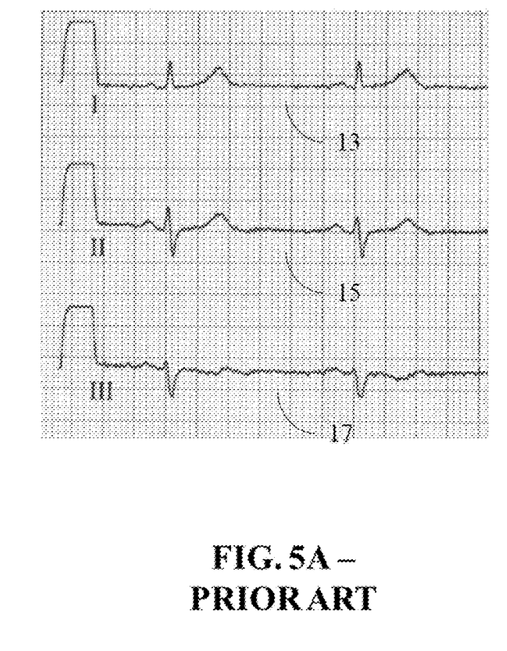
FIG. 5A shows a regular ECG trace from a standard 3-lead ECG when used with electrodes in the standard position.
Figure 5B:
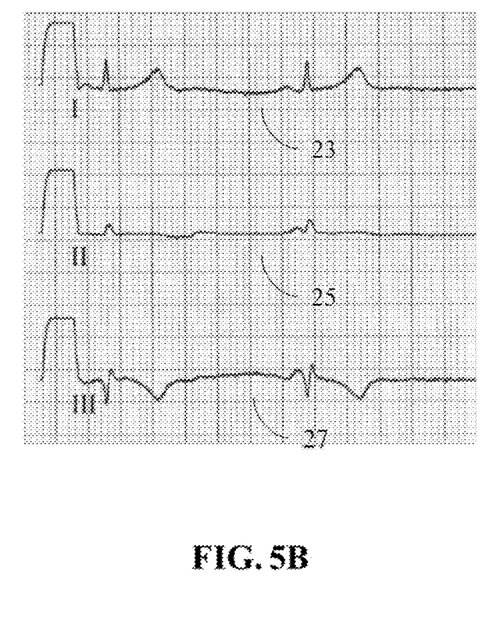
FIG. 5B shows a typical pre-transformation ECG trace from a device of some embodiments of the present invention.
Figure 5C:
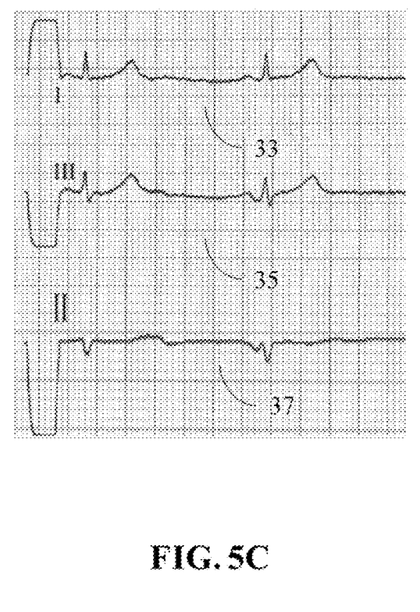
FIG. 5C shows a transformed version of the pre-transformation ECG trace.

Reference is made now to FIGS. 5A-5C. FIG. 5A shows traces of Lead I 13, Lead II 16, and Lead III 17 from a leg-attached three-lead ECG 10 of FIG. 3. FIG. 5B shows traces of Lead I 23, Lead II 26, and Lead III 27 from the oral 3-lead ECG device 20 of FIG. 4. The waveforms from Lead I of both ECGs (trace 13 and trace 23) are identical, inasmuch as both derive from signal between left-hand and right-hand electrodes. However, Leads II and III of the oral 3-lead ECG 20 have become transposed and the polarity of the signal on each has become reversed from those of the leg-attached 3-lead ECG 10—such that the waveform of trace 27 is the inverse polarity of trace 16 and the waveform of trace 26 is the inverse polarity of trace 17. These transformations are a consequence of the reverse in direction that has taken place of the signal from each of the two hands via the heart to mouth contact 26, when compared to the standard configuration.

The transformation that therefore needs to be performed in order to transform the electrical signals received from the ECG device 20 of the present invention, shown in FIG. 5B, into the standard traces shown in FIG. 5A comprises the following steps:

1. Leave Lead I of the trace without change.
2. Transpose the order of Lead II 25 and Lead III 26.
3. Reverse the polarity and increase the gain of the waveform of Lead II 25, resulting in transposed, reversed, amplified Lead II 37 in FIG. 5C.
4. Reverse the polarity of the waveform of Lead III, resulting in transposed, reversed Lead III 35 in FIG. 5C.

The traces of the transformed waveforms from the oral 3-lead ECG 20, shown in FIG. 5C—traces 33, 35, and 37 are substantively equivalent to the traces of the leg-attached 3-lead ECG 10 traces 13, 15, and 17 shown in FIG. 5A. This enables an ECG display to be produced using the device 20 of the present invention which mimics traces from a standard, leg-attached ECG 10, despite the fact that the oral device 20 is connected and used in a 245 different manner than the leg-attached device 10.

Advantageously, by providing ECG trace displays which mimic a standard one, the display can readily be understood by a physician and/or remote physician viewing it, and also be interpreted by software programs which interpret ECG traces. Such programs are available over the Internet, enabling ECG interpretation to be performed in the cloud.

Advantageously, implementing a 3-lead ECG device in accordance with the current invention makes the device very simple to use as (a) the thermometer shape is familiar and convenient, and (b) the need to run a cable down to the left leg is obviated.

Unlike ECG devices like the Apple Watch or the KardiaMobile ECG product (AliveCor, Mountain View, CA, USA), where the patient places a finger on an electric plate—and therefore the quality of the skin-electrode contact is subject to shaking of the finger—the device 20 of the present invention is grasped between the forefinger and the thumb, such that the finger against the electrode is held there stably due to the counterposing force from the thumb underneath the device. Advantageously, this stable connection between the electrode(s) and the finger(s) represents an additional synergy between the thermometer shape and the ECG implementation therein.

Additional advantages deriving from the thermometer-based shape of devices 20, 100 of the present invention include the ability to measure vital signs and other physiological data as measured using sensors mounted on or within the body of the device together with the ECG signals gathered by the device 20, 100. The sensors can include any combination of the following: an oral temperature sensor implemented within the oral tip of the device, a pulse-oximetry sensor, a respiratory rate sensor, a skin temperature sensor, a body impedance sensor, a galvanic skin response sensor and a blood-flow sensor.

In a preferred embodiment of the device, the output is displayed on a smartphone or PC connected to the device 20, 100 either wirelessly over Bluetooth or WiFi, etc., or via a wired connection. This display may contain a 1-lead ECG output (not shown) or a transformed 3-lead ECG trace as per FIG. 5C, together with any combination of the vital-signs readings taken using the additional sensors as listed above.

Advantageously, the combination of providing an ECG trace while also providing additional medical data such as temperature and pulse oximetry enables the patient to perform an extensive and comprehensive medical check during one simple deployment of the device 20.

Figure 6:
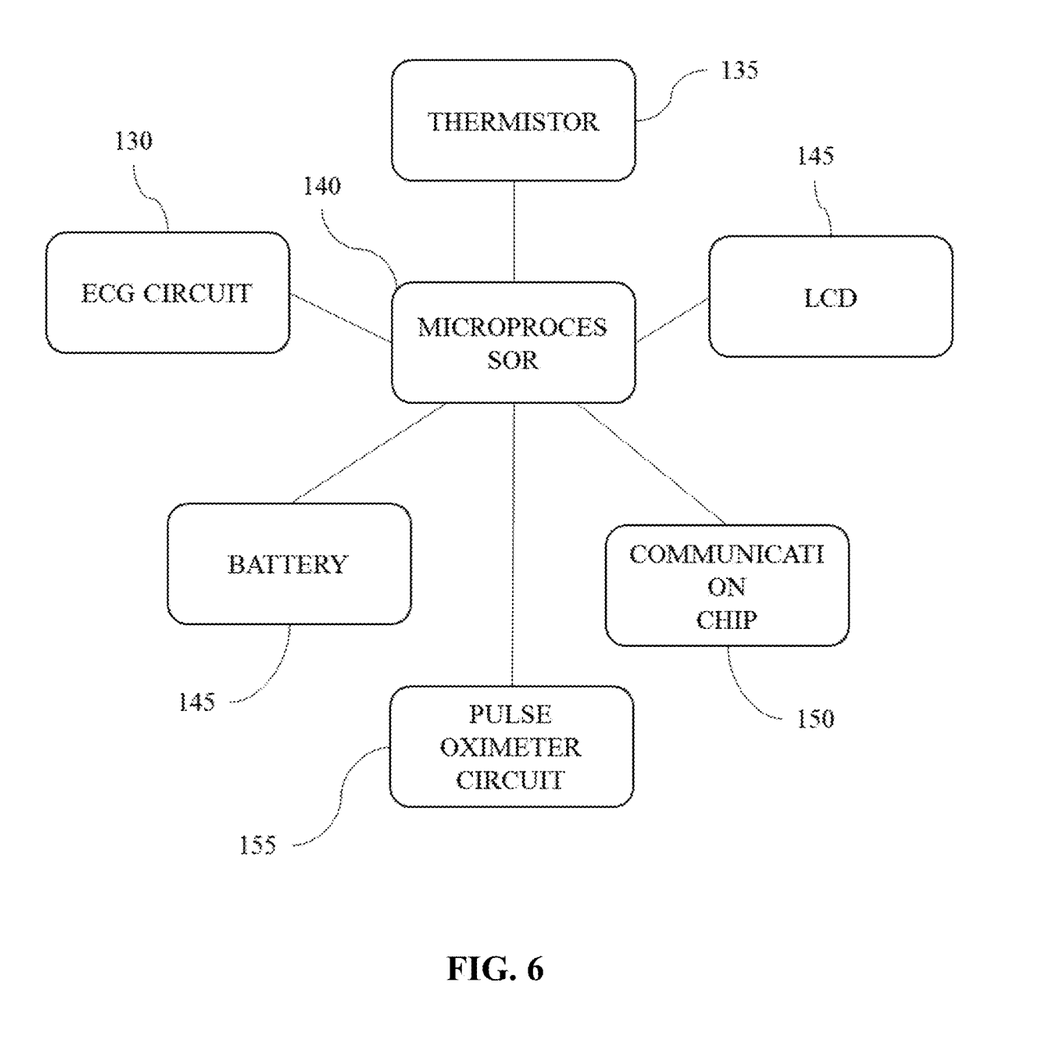
FIG. 6 shows a functional block diagram of oral ECG/thermometer devices, according some embodiments of the invention.

Reference is now made to FIG. 6, showing an electronic block diagram according to some embodiments of an oral 1-lead ECG/thermometer 100 and an oral 3-lead ECG device 20. An ECG circuit 130 for a 1-lead device 100 may comprise a MAX86150 PPG/ECG bio-sensor module from Maxim Integrated (San Jose, USA). Suitable chips for implementing a 3-lead ECG device 20 include the ADS1293 chip from Texas Instruments (Texas, USA). Alternatively, the electrode pairs of each of the leads of the 3-lead device 20 may be read out serially by a 1-lead ECG chip.

For embodiments comprising a thermometer, a thermistor 135 for temperature sensing may comprise an MF51E2252F3950C thermistor from Cantherm (Montreal, Canada). A microprocessor 140 may comprise one of the PSoC 63 family MCU from Cypress Semiconductors (San Jose, California, USA). Some embodiments comprise a communication chip 150, for wireless or wired communication with an external device. However, in preferred embodiments the microprocessor 140 comprises built-in communication function, such as Bluetooth Low Energy (BLE), such that a separate communication chip 150 is not required. In embodiments with a pulse oximetry sensor 127, electronic components further comprise a pulse oximeter circuit 155.

The invention claimed is:

1. An oral 3-lead ECG device in the shape of a digital-thermometer comprising three contact electrodes:
   a left-hand contact electrode configured for contact with the left hand of a subject;
   a right-hand contact electrode configured for contact with the right hand of the subject; and
   a mouth contact electrode disposed on a metallic tip of said device, configured for contact with the patient's mouth;
   wherein the device further comprises a processor configured to perform a transformation of signals from the right-hand contact electrode and left-hand contact electrode, terminating at the mouth-contact electrode, thereby producing ECG traces mimicking traces of a standard ECG whose right-hand contact electrode and left-hand contact electrode terminate at a left-leg electrode.

2. The oral 3-lead ECG device of claim 1, wherein the processor is configured to perform the transformation by
   transposing the order of right-hand contact electrode and left-hand contact electrode; reversing the polarity and increasing the gain of waveform of right-hand contact electrode, and reversing the polarity of the waveform of the left-hand contact electrode.

3. The oral 3-lead ECG device of claim 1, further comprising one or more sensors from a group consisting of an oral temperature sensor disposed in said metallic tip, a pulse-oximetry sensor, a respiratory rate sensor, a skin temperature sensor, a body impedance sensor, a galvanic skin response sensor, and a blood-flow sensor.

4. The oral 3-lead ECG device of claim 1, wherein the pulse-oximetry sensor is positioned proximate or opposite to the left-hand contact electrode or right-hand contact electrode.

5. The oral 3-lead ECG device of claim 1, further comprising a communications module enabling the display of said ECG trace on an external device (e.g., smartphone or computer).

6. The oral 3-lead ECG device of claim 5, wherein said display further comprises sensor data from one or more sensors from the group consisting an oral temperature sensor, a pulse-oximetry sensor, a respiratory rate sensor, a skin temperature sensor, a body impedance sensor, a galvanic skin response sensor, and a blood-flow sensor; and said oral 3-lead ECG device further comprises said one or more sensors.

7. The oral 3-lead ECG device of claim 5, further comprising a data-transfer agent module installed in the external device, said data-transfer agent module configured to transmit said ECG and/or sensor data over the Internet to a remote device (e.g., for storage and/or analysis).

8. The oral 3-lead ECG device of claim 7, further comprising a remote agent module installed in the remote device; the remote agent module is configured to perform medical analysis of the transmitted ECG data and/or the transmitted sensor data.

9. The oral 3-lead ECG device of claim 1, further comprising an ECG circuit with three ECG channels configured for simultaneously sampling the three leads.

10. The oral 3-lead ECG device of claim 1, further comprising an ECG circuit with one ECG channel, said ECG circuit configured for simultaneously sampling the three leads.

11. A method for transformation of the signals from ECG leads of an oral 3-lead ECG, comprising steps of
    obtaining ECG traces from oral 3-lead ECG device of claim 1;
    transposing the order of right-hand contact electrode and left-hand contact electrode; reversing the polarity and increasing the gain of the waveform of right-hand contact electrode and reversing the polarity of the waveform of left-hand contact electrode.

* * * * *